US011384092B2

(12) United States Patent
Tu et al.

(10) Patent No.: US 11,384,092 B2
(45) Date of Patent: Jul. 12, 2022

(54) DIANHYDRIDE COMPOUND HAVING RIGID ALICYCLIC FLUORINE-CONTAINING STRUCTURE, AND PREPARATION METHOD AND USE THEREOF

(71) Applicant: HUAZHONG UNIVERSITY OF SCIENCE AND TECHNOLOGY, Hubei (CN)

(72) Inventors: Guoli Tu, Hubei (CN); Fu Li, Hubei (CN); Yao Wang, Hubei (CN)

(73) Assignee: HUAZHONG UNIVERSITY OF SCIENCE AND TECHNOLOGY, Hubei (CN)

( * ) Notice: Subject to any disclaimer, the term of this patent is extended or adjusted under 35 U.S.C. 154(b) by 589 days.

(21) Appl. No.: 16/465,152

(22) PCT Filed: Dec. 28, 2018

(86) PCT No.: PCT/CN2018/124730

§ 371 (c)(1),
(2) Date: May 30, 2019

(87) PCT Pub. No.: WO2020/000968

PCT Pub. Date: Jan. 2, 2020

(65) Prior Publication Data

US 2021/0094965 A1 Apr. 1, 2021

(30) Foreign Application Priority Data

Jun. 25, 2018 (CN) ........................ 201810664515.X

(51) Int. Cl.
*C07D 493/04* (2006.01)
*C08G 73/10* (2006.01)
*C08J 5/18* (2006.01)

(52) U.S. Cl.
CPC ....... *C07D 493/04* (2013.01); *C08G 73/1067* (2013.01); *C08J 5/18* (2013.01); *C08J 2379/08* (2013.01)

(58) Field of Classification Search
None
See application file for complete search history.

(56) References Cited

U.S. PATENT DOCUMENTS 3,702,318 A 11/1972 Browning

FOREIGN PATENT DOCUMENTS

| | | |
|---|---|---|
| CN | 103113687 | 5/2013 |
| CN | 103524767 | 1/2014 |
| CN | 103524768 | 1/2014 |
| JP | S58124789 | 7/1983 |
| JP | S58124790 | 7/1983 |
| JP | 2014118568 | 6/2014 |

OTHER PUBLICATIONS

Li et al. “High Performance Soluble Polyimides from Ladder-Type Fluorinated Dianhydride with Polymorphism” Polymers, vol. 10, Article 546, pp. 1-17. (Year: 2018).*

“Office Action of Japan Counterpart Application”, dated Sep. 8, 2020, p. 1-p. 6.

Rajendra P. Singh, et al., “Synthesis and characterization of novel trifluoromethyl-containing alcohols with Ruppert’s reagent,” Journal of Fluorine Chemistry, vol. 133, Jan. 2012, pp. 1-8.

* cited by examiner

*Primary Examiner* — Joseph R Kosack
(74) *Attorney, Agent, or Firm* — JCIPRNET

(57) ABSTRACT

The present invention relates to the technical field of new materials, and provides a dianhydride compound having a rigid alicyclic fluorine-containing structure, and a preparation method and use thereof. The preparation method includes a first step of subjecting 2,3,6,7-tetramethylanthracene-9,10-dione to a nucleophilic addition reaction, to obtain ((2,3,6,7-tetramethyl-9,10-bis(trifluoromethyl)-9,10-dihydroanthracene-9,10-diyl)bis(oxy))bis(trimethylsilicane); a second step of converting the trimethylsiloxane on the product obtained in the first step into a hydroxyl group; and a third step of replacing the hydroxyl group on the product obtained in the second step by F, Cl, $CF_3$ or a phenyl ring, and then oxidizing and dehydrating into an anhydride to obtain a dianhydride compound.

10 Claims, 10 Drawing Sheets

DIANHYDRIDE COMPOUND HAVING RIGID ALICYCLIC FLUORINE-CONTAINING STRUCTURE, AND PREPARATION METHOD AND USE THEREOF

CROSS-REFERENCE TO RELATED APPLICATION

This application is a 371 application of the International PCT application serial no. PCT/CN2018/124730, filed on Dec. 28, 2018, which claims the priority benefits of China application no. 201810664515.X, filed on Jun. 25, 2018. The entirety of each of the above-mentioned patent applications is hereby incorporated by reference herein and made a part of this specification.

BACKGROUND OF THE INVENTION

1. Field of the Invention

The present invention relates to the technical field of new materials, and in particular, to a new dianhydride compound having a rigid alicyclic fluorine-containing structure, and a synthesis method and use thereof.

2. Description of Related Art

In recent years, with the accelerated upgrade in the display industry, the demand for large-size flexible organic light-emitting diodes (OLEDs) will grow exponentially, which will also drive the development of and demand for flexible substrates. At present, the mostly often used flexible substrates are: polyethylene terephthalate (PET), polycarbonate (PC), polyethylene naphthalate (PEN) and other engineering plastics. The above engineering plastics have a high transmittance (>85%), but fatal disadvantages of poor heat resistance (Tg <120° C.) and poor solvent resistance. The preparation of large-size flexible OLEDs requires high-temperature processing, and it is obvious that the above-mentioned engineering plastics cannot satisfy this condition. Therefore, flexible transparent polyimide films (PIs) with excellent heat resistance and solvent resistance have become an optimum choice for a desirable flexible OLED substrate.

The traditional aromatic polyimide is prepared by copolymerizing an aromatic dianhydride monomer with strong electron-withdrawing ability and an aromatic diamine monomer with strong electron donating ability. The polymer backbone is closely packed, and there is strong conjugation between the aromatic rings, such that strong intrachain and interchain charge transfer complex effects exist for the molecular chain of the polyimide. The strong interchain interaction between the rings gives the above-mentioned excellent properties of PIs, and also causes the defects of poor solution processability, and poor optical permeability of aromatic PIs, affecting the application of PIs in the display field.

In the literature entitled "Colorless polyimides derived from 2R, 5R, 7S, 10S-naphthanetetracarboxylic dianhydride", a novel alicyclic dianhydride 2R,5R,7S,10S-naphthanetetracarboxylic dianhydride (HNTDA) is synthesized. It is found that compared with the PIs prepared from hydrogenated pyromellitic dianhydride (HPMDA), the HNTDA-based PIs exhibit excellent thermodynamic properties, and the rigid fused naphthalene tetracarboxydiimide moiety significantly weakens the intermolecular and intramolecular Interaction, thereby improving the optical properties of the film while maintaining good thermal stability. However, if the CTE value of the film is greater than 40 ppm $K^{-1}$ and the CTE value is large, the PI film will warp, crack or delamination when heated, thus limiting the application of the PI film.

In the literature entitled "Flexible QLED and OPV based on transparent polyimide substrate with rigid alicyclic asymmetric isomer", an indandiamine having a rigid semi-alicyclic structure is introduced onto the molecular backbone, followed by polymerization with five different commercially available dianhydrides, to obtain a series of PIs. The performance test proves that the introduction of the rigid alicyclic structure effectively inhibits the formation of the CTC effect and improves the optical transmittance of the film on one hand. On the other hand, the alicyclic structure is directly attached to the benzene ring, avoiding the problem of poor heat resistance of the traditional full-alicyclic structure. In addition, using CPI-1 as a flexible substrate, corresponding OPV and QLED devices are fabricated, which show good device efficiency. The improvement of the alicyclic structure on the optical properties of polyimide is obvious, but breaking the conjugation, weakening the interchain interaction and the CTC effect cause the heat resistance of PIs to decrease, as can be seen from the structure reported above. Therefore, it is difficult to achieve the performance requirements for flexible substrates in the display field simply by modifying the polyimide by introducing an alicyclic structure.

In the Chinese Patent Publication No. CN105131286A, a polyimide is prepared by thermal imidization with an aromatic dianhydride compound 3,3',4,4'-biphenyltetracarboxylic dianhydride (sBPDA) or an alicyclic dianhydride compound 1,2,3,4-cyclobutenetetracarboxylic dianhydride (CBDA) and an aromatic diamine compound as raw materials. By adjusting the ratio of sBPDA and CBDA or 1,3-dimethyl-1,2,3,4-cyclobutanetetracarboxylic dianhydride (MCBDA), the heat stability and optical transparency of the polyimide film substrate can be adjusted.

However, the glass transition temperature Tg of the polyimide film prepared by the method is less than 350° C.

4,4'-(hexafluoroisopropylidene)diphthalic anhydride (6FDA) has a sp3 hybridized quaternary carbon structure which increases the degree of molecular twist. In addition, the steric hindrance imparted by the $CF_3$ group can well destroy the stacking degree and stacking density of the molecular chain, thereby reducing the intrachain and interchain interaction. Therefore, the formation of the charge transfer complex (CTC) of the polymer has a large inhibitory effect, and thus the color of the relevant film become light, making the polyimide more suitable for certain specific applications. However, the rigidity of the 6FDA molecule is weak, resulting in a large linear coefficient of thermal expansion (CTE) of polyimide. 1,2,4,5-cyclohexanetetracarboxylic dianhydride (HPMDA), as an aliphatic dianhydride monomer, can significantly reduce the CTC effect and improve transmittance of PIs. However, the spatial isomerism of HPMDA molecules affects the polymerization reactivity In addition, the HPMDA-based polyimide shows good thermal stability and weak oxidation resistance. The most notorious disadvantage is that it is prone to yellowing at high temperatures.

In the field of flexible displays, a desirable substrate requires a glass transition temperature of above 400° C. and a CTE value of below 20 ppm $K^{-1}$. In the present invention, by combining the advantages of 6FDA and HPMDA, a dianhydride 9,10-difluoro-9,10-bis(trifluoromethyl)-9,10-dihydroanthracene-2,3,6,7-tetracarboxylic dianhydride (8FDA) having a rigid semi-alicyclic ring and a trifluoromethyl group and substituted with fluorine is designed and synthesized.

SUMMARY OF THE INVENTION

Accordingly, to solve the technical problem of low glass transition temperature, high linear coefficient of thermal expansion and poor thermal stability of polymers containing a dianhydride monomer existing in the prior art, the present invention is directed to a dianhydride compound having a rigid alicyclic fluorine-containing structure, and a preparation method and use thereof.

According to a first aspect of the present invention, a dianhydride compound having a rigid cycloaliphatic fluorine-containing structure is provided, which is represented by a structural Formula I below:

Formula (I)

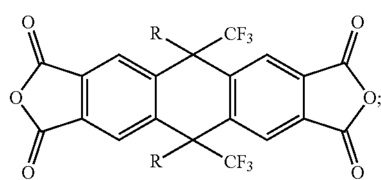

where

R is F, Cl, $CF_3$ or (phenyl).

According to another aspect of the present invention, a method for preparing a dianhydride compound having a rigid cycloaliphatic fluorine-containing structure is provided, which includes the steps of:

(1) adding trimethyl(trifluoromethyl)silicane or triethyl (trifluoromethyl) silicane to a solution of 2,3,6,7-tetramethylanthracene-9,10-dione, cooling, adding a catalyst A, mixing well until uniform, then heating the reaction temperature to 30-50° C., and reacting for 6-24 hrs, to allow the 2,3,6,7-tetramethylanthracene-9,10-dione to undergo a nucleophilic addition reaction, to obtain ((2,3,6,7-tetramethyl-9,10-bis (trifluoromethyl)-9,10-dihydroanthracene-9,10-diyl)bis (oxy))bis(trimethylsilicane);

(2) dissolving the ((2,3,6,7-tetramethyl-9,10-bis(trifluoromethyl)-9,10-dihydroanthracene-9,10-diyl)bis(oxy))bis (trimethylsilicane) obtained in the step (1) and then reacting for 0.5-5 h in an acidic environment at a temperature of 25-80° C., to convert the trimethylsiloxane on the ((2,3,6,7-tetramethyl-9,10-bis(trifluoromethyl)-9,10-dihydroanthracene-9,10-diyl)bis(oxy))bis(trimethylsilicane) into a hydroxyl group, to obtain 2,3,6,7-tetramethyl-9,10-bis(trifluoromethyl)-9,10-dihydroanthracene-9,10-diol;

(3) dissolving the 2,3,6,7-tetramethyl-9,10-bis(trifluoromethyl)-9,10-dihydroanthracene-9,10-diol obtained in the step (2), adding diethylaminosulfur trifluoride or bis(2-methoxyethyl)aminosulfur trifluoride dropwise in an ice bath, and reacting for 12-15 h, to obtain 9,10-difluoro-2,3,6,7-tetramethyl-9,10-bis(trifluoromethyl)-9,10-dihydroanthracene;

or (3) dissolving the 2,3,6,7-tetramethyl-9,10-bis(trifluoromethyl)-9,10-dihydroanthracene-9,10-diol obtained in the step (2), adding acetyl chloride, and reacting for 8-12 h at 70-80° C., to obtain 9,10-dichloro-2,3,6,7-tetramethyl-9,10-bis(trifluoromethyl)-9,10-dihydroanthracene;

or (3) dissolving the 2,3,6,7-tetramethyl-9,10-bis(trifluoromethyl)-9,10-dihydroanthracene-9,10-diol obtained in the step (2), adding hydrogen halide and trifluoromethyl halide, and reacting for 15-30 h, to obtain 2,3,6,7-tetramethyl-9,9',10,10'-tetrakis(trifluoromethyl)-9,10-dihydroanthracene;

or (3) dissolving the 2,3,6,7-tetramethyl-9,10-bis(trifluoromethyl)-9,10-dihydroanthracene-9,10-diol obtained in the step (2), followed by a first step of adding phosphorus tribromide, or adding hydrogen bromide and a catalyst B, and reacting for 12-24 h at 40-60° C., to converting the hydroxyl group on the 2,3,6,7-tetramethyl-9,10-bis(trifluoromethyl)-9,10-dihydroanthracene-9,10-diol into a bromine atom, to obtain 9,10-dibromo-2,3,6,7-tetramethyl-9,10-bis (trifluoromethyl)-9,10-dihydroanthracene; and a second step of adding phenylmagnesium bromide and a catalyst C, or adding phenylboronic acid and a catalyst D, and reacting for 8-15 h at 75-90° C., to replace the bromine atom on the 9,10-dibromo-2,3,6,7-tetramethyl-9,10-bis(trifluoromethyl)-9,10-dihydroanthracene by a phenyl group, to obtain 2,3,6,7-tetramethyl-9,10-diphenyl-9,10-bis(trifluoromethyl)-9,10-dihydroanthracene;

(4) dissolving the 9,10-difluoro-2,3,6,7-tetramethyl-9,10-bis(trifluoromethyl)-9,10-dihydroanthracene, 9,10-dichloro-2,3,6,7-tetramethyl-9,10-bis(trifluoromethyl)-9,10-dihydroanthracene, 2,3,6,7-tetramethyl-9,9',10,10'-tetrakis (trifluoromethyl)-9,10-dihydroanthracene, or 2,3,6,7-tetramethyl-9,10-diphenyl-9,10-bis(trifluoromethyl)-9,10-dihydroanthracene obtained in the step (3), adding an oxidant, reacting for 12-15 h at 90-110° C., filtering under suction, rotary drying the filtrate, dissolving the product, and acidifying, to obtain 9,10-difluoro-9,10-bis(trifluoromethyl)-9,10-dihydroanthracene-2,3,6,7-tetracarboxylic acid, 9,10-dichloro-9,10-bis(trifluoromethyl)-9,10-dihydroanthracene-2,3,6,7-tetracarboxylic acid, 9,9',10,10'-tetrakis (trifluoromethyl)-9,10-dihydroanthracene-2,3,6,7-tetracarboxylic acid or 9,10-diphenyl-9,10-bis(trifluoromethyl)-9,10-dihydroanthracene-2,3,6,7-tetracarboxylic acid; and (5) dehydrating the 9,10-difluoro-9,10-bis(trifluoromethyl)-9,10-dihydroanthracene-2,3,6,7-tetracarboxylic acid, 9,10-dichloro-9,10-bis(trifluoromethyl)-9,10-dihydroanthracene-2,3,6,7-tetracarboxylic acid, 9,9',10,10'-tetrakis (trifluoromethyl)-9,10-dihydroanthracene-2,3,6,7-tetracarboxylic acid or 9,10-diphenyl-9,10-bis(trifluoromethyl)-9,10-dihydroanthracene-2,3,6,7-tetracarboxylic acid obtained in the step (4) into an anhydride, to obtain 9,10-difluoro-9,10-bis(trifluoromethyl)-9,10-dihydroanthracene-2,3,6,7-tetracarboxylic dianhydride, 9,10-dichloro-9,10-bis(trifluoromethyl)-9,10-dihydroanthracene-2,3,6,7-tetracarboxylic dianhydride, 9,9',10,10'-tetrakis(trifluoromethyl)-9,10-dihydroanthracene-2,3,6,7-tetracarboxylic dianhydride or 9,10-diphenyl-9,10-bis(trifluoromethyl)-9,10-dihydroanthracene-2,3,6,7-tetracarboxylic dianhydride.

Preferably, the catalyst A in the step (1) is cesium fluoride, tetrabutylammonium fluoride or tris(dimethylamino)sulfonium difluorotrimethylsilicate; the catalyst B in the step (3) is concentrated sulfuric acid; the catalyst C in the step (3) is 1,3-bis(diphenylphosphinopropane)nickel dichloride, or a mixture of palladium acetate and triphenylphosphine; the catalyst D in the step (3) is a mixture of tetrakis(triphenylphosphine)palladium and potassium carbonate, or a mixture of palladium and potassium carbonate, or a mixture of sodium tetrachloropalladate and potassium carbonate; and the oxidant in the step (4) is potassium permanganate or chromium trioxide.

Preferably, the hydrogen halide in the step (3) is hydrogen bromide, hydrogen iodide or hydrogen chloride; and the trifluoromethyl halide in the step (3) is trifluoromethyl bromide, trifluoromethyl iodide or trifluoromethyl chloride.

Preferably, the ratio of amount of substances of 2,3,6,7-tetramethylanthracene-9,10-dione, trimethyl(trifluoromethyl)silicane, and the catalyst A in the step (1) is 1:(2-3.5):(0.01-0.05).

Preferably, the ratio of amount of substances of 2,3,6,7-tetramethyl-9,10-bis(trifluoromethyl)-9,10-dihydroanthracene-9,10-diol to diethylaminosulfur trifluoride, or to bis(2-methoxyethyl)aminosulfur trifluoride in the step (3) is 1:(2-3.5).

Preferably, the ratio of amount of substances of 9,10-difluoro-2,3,6,7-tetramethyl-9,10-bis(trifluoromethyl)-9,10-dihydroanthracene, 9,10-dichloro-2,3,6,7-tetramethyl-9,10-bis(trifluoromethyl)-9,10-dihydroanthracene, 2,3,6,7-tetramethyl-9,9',10,10'-tetrakis(trifluoromethyl)-9,10-dihydroanthracene or 2,3,6,7-tetramethyl-9,10-diphenyl-9,10-bis(trifluoromethyl)-9,10-dihydroanthracene to the oxidant in the step (4) is 1:(10-12).

According to another aspect of the present invention, use of the dianhydride compound having a rigid cycloaliphatic fluorine-containing structure in the preparation of a polyimide material is provided.

According to another aspect of the present invention, a method for preparing a polyimide film is provided, which includes the steps of:

(1) dissolving a diamine, adding the dianhydride compound having a rigid alicyclic fluorine-containing structure, and reacting for 10-30 h at 25-35° C., to obtain a polyamic acid solution; and (2) dispersing the polyamic acid solution obtained in the step (1) uniformly on the surface of the substrate, heating to volatilize the solvent in the polyamic acid solution, and further heating to cause dehydration and cyclization of the polyamic acid to obtain a polyimide film.

According to another aspect of the present invention, a polyimide film prepared through the method is provided.

In general, compared with the prior art, the following technical advantages can be achieved with the above technical solutions conceived in the present invention.

(1) The semi-alicyclic segment of 1,4-cyclohexadiene in the dianhydride compound having a rigid alicyclic fluorine-containing structure provided in the present invention can effectively destroy the degree of conjugation of the polymer chain, so the charge transfer complex effect is effectively suppressed, and the optical performance is improved. Moreover, the spatial effect of the fluorine-containing group and the alicyclic structure can increase the free volume (FFV) of the polymer segment and improve the solution processability of the polyimide film of the dianhydride compound having a rigid alicyclic fluorine-containing structure. In addition, the rigid alicyclic structure can ensure the rigidity of the molecular chain and reduce the mobility of the segment, thereby increasing the glass transition temperature and thermal stability. The rigid structure can reduce the linear coefficient of thermal expansion of the polyimide based on the dianhydride compound having a rigid alicyclic fluorine-containing structure according to the present invention. Therefore, it can be used to prepare a transparent high-temperature resistant polyimide film having low linear coefficient of thermal expansion. The dianhydride compound having a rigid alicyclic fluorine-containing structure according to the present invention has simple structure, and has wide application value for the development of transparent polyimide films.

(2) The dianhydride having a rigid alicyclic fluorine-containing structure of the present invention has a rigid alicyclic ring and a fluorine-containing structure. When used in the preparation of a polymer material, the dianhydride having a rigid alicyclic fluorine-containing structure of the present invention can improve the light transmittance, reduce the dielectric constant and water absorption, and maintain good thermal stability and dimensional stability of the material, so it is suitable for the preparation of a flexible transparent polyimide film.

(3) The method for preparing a dianhydride compound having a rigid alicyclic fluorine-containing structure is simple, the reaction conditions are mild, the reaction raw materials are readily available, the cost is low, and the type of organic solvents used are less, thus reducing the environmental pollution.

(4) In the present invention, by combining the advantages of 4,4'-(hexafluoroisopropylidene)diphthalic anhydride (6FDA) and 1,2,4,5-cyclohexane tetracarboxylic dianhydride (HPMDA), a dianhydride 9,10-difluoro-9,10-bis(trifluoromethyl)-9,10-dihydroanthracene-2,3,6,7-tetracarboxylic dianhydride having a rigid semi-alicyclic ring and a trifluoromethyl group and substituted with fluorine is synthesized. The material has high glass transition temperature and low linear coefficient of thermal expansion, and is an ideal dianhydride monomer material for preparing polyimide films.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIG. 1(*b*) is a $^{13}$C NMR spectrum of ((2,3,6,7-tetramethyl-9,10-bis(trifluoromethyl)-9,10-dihydroanthracene-9,10-diyl)bis(oxy))bis(trimethylsilicane) synthesized in Step 1 of Example 1.

FIG. 2(*b*) is a $^{13}$C NMR spectrum of 2,3,6,7-tetramethyl-9,10-bis(trifluoromethyl)-9,10-dihydroanthracene-9,10-diol synthesized in Step 2 of Example 1.

FIG. 3(*b*) is a $^{13}$C NMR spectrum of 9,10-difluoro-2,3,6,7-tetramethyl-9,10-bis(trifluoromethyl)-9,10-dihydroanthracene synthesized in Step 3 of Example 1.

FIG. 4(*b*) is a $^{13}$C NMR spectrum of 9,10-difluoro-9,10-bis(trifluoromethyl)-9,10-dihydroanthracene-2,3,6,7-tetracarboxylic acid synthesized in Step 4 of Example 1.

and FIG. 5(*b*) is a $^{13}$C NMR spectrum of 9,10-difluoro-9,10-bis(trifluoromethyl)-9,10-dihydroanthracene-2,3,6,7-tetracarboxylic dianhydride synthesized in Step 5 of Example 1.

DESCRIPTION OF THE EMBODIMENTS

Figure 1A:
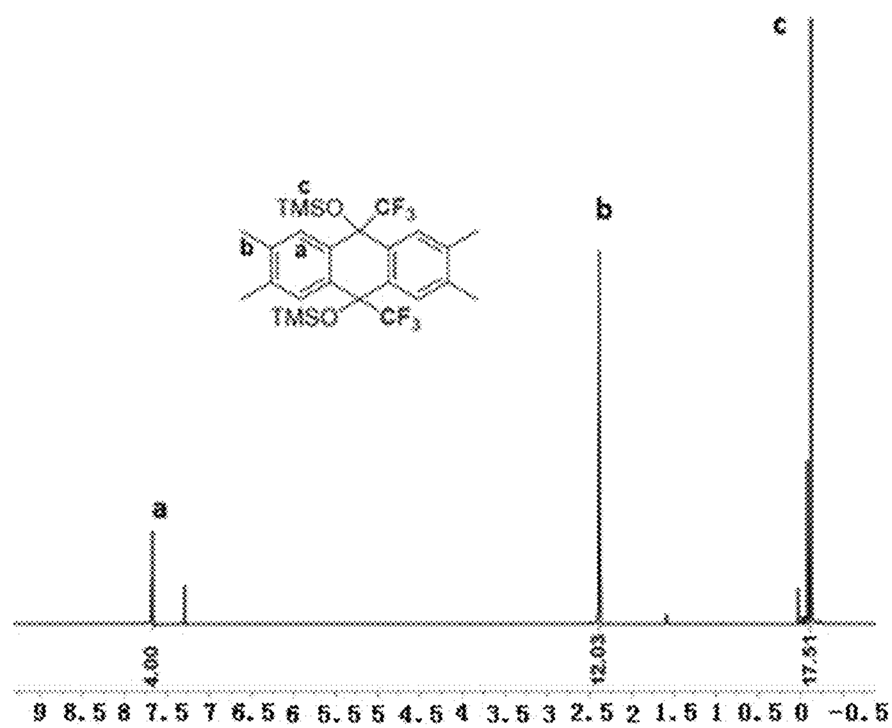
FIG. 1(*a*) is a $^1$H NMR spectrum of ((2,3,6,7-tetramethyl-9,10-bis(trifluoromethyl)-9,10-dihydroanthracene-9,10-diyl)bis(oxy))bis(trimethylsilicane) synthesized in Step 1 of Example 1.

Reference will now be made in detail to the present preferred embodiments of the invention, examples of which are illustrated in the accompanying drawings. Wherever possible, the same reference numbers are used in the drawings and the description to refer to the same or like parts.

To make the objects, technical solutions, and advantages of the present invention clearer, the present invention is described in further detail with reference to accompanying drawings and examples. It should be understood that the specific examples described herein are merely provided for illustrating, instead of limiting the present invention. In addition, the technical features involved in various embodiments of the present invention described below can be combined with each other as long as they do not form a conflict with each other.

EXAMPLE 1

Figure 9:
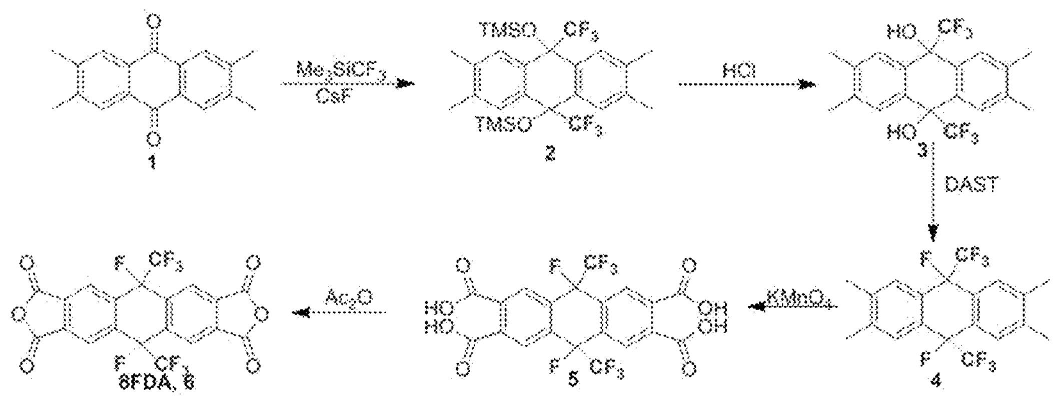
FIG. 9 is a schematic view showing a process for preparing the compound 9,10-difluoro-9,10-bis(trifluoromethyl)-9,10-dihydroanthracene-2,3,6,7-tetracarboxylic dianhydride.

A dianhydride compound having a rigid alicyclic fluorine-containing structure, that is, 9,10-difluoro-9,10-bis(trifluoromethyl)-9,10-dihydroanthracene-2,3,6,7-tetracarboxylic dianhydride (8FDA) is prepared through a process as shown in FIG. 9.

Step 1:2,3,6,7-tetramethylanthracene-9,10-dione (40.00 g, 151.33 mmol, 1.00 eq.) was suspended in THF (400 mL) at room temperature (r.t.) and trimethyl(trifluoromethyl) silicane (49.21 mL, 332.93 mmol, 2.20 eq.) was added. The suspension was cooled to 0° C., and CsF (459.74 mg, 3.03 mmol, 0.02 eq.) was added. After stirring for 10 minutes, the reaction mixture was warmed to room temperature and stirred for 1.5 hours. The reaction mixture was filtered and the remaining yellow solid was washed with diethyl ether (25 mL). The crude product was separated by column chromatography (n-pentane to n-pentane/MTBE 15:1), to obtain the compound ((2,3,6,7-tetramethyl-9,10-bis(trifluoromethyl)-9,10-dihydroanthracene-9,10-diyl)bis(oxy))bis (trimethylsilicane) (16.6 g, 30.27 mmol, 20%) as a white solid. $^1$H NMR (400 MHz, CDCl3) δ7.67 (s, 1H), 2.38 (d, J=3.3 Hz, 3H), −0.10 (d, J=15.5 Hz, 5H).

Figure 1B:
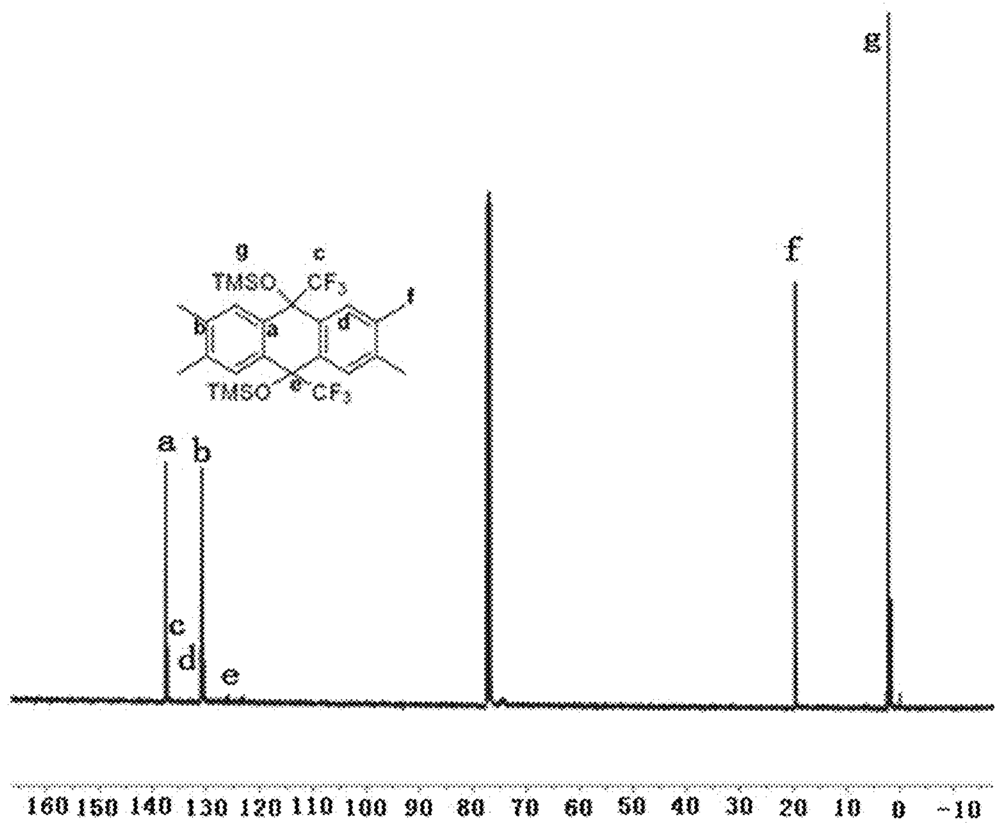

FIG. 1(*a*) is a $^1$H NMR spectrum of ((2,3,6,7-tetramethyl-9,10-bis(trifluoromethyl)-9,10-dihydroanthracene-9,10-diyl)bis(oxy))bis(trimethylsilicane) synthesized in Step 1 of Example 1; and FIG. 1(*b*) is a 13C NMR spectrum of ((2,3,6,7-tetramethyl-9,10-bis(trifluoromethyl)-9,10-dihydroanthracene-9,10-diyl)bis(oxy))bis(trimethylsilicane) synthesized in Step 1 of Example 1. As can be seen from FIG. 1, $^1$H NMR (600 MHz, $CDCl_3$) δ7.67 (s, 4H), 2.38 (d, J=3.3 Hz, 12H), −0.12 (d, J=14.4 Hz, 18H). $^{13}$C NMR (150 MHz, CDCl3) 137.56, 137.22, 131.04-130.69, 130.40, 125.87, 19.67, 2.19, 1.99-1.54. $^{19}$F NMR (565 MHz, $CDCl_3$) δ−78.39 (s, 6F). Therefore, the compound obtained in Step 1 is (2,3,6,7-tetramethyl-9,10-bis(trifluoromethyl)-9,10-dihydroanthracene-9,10-diyl)bis(oxy))bis(trimethylsilicane).

Step 2: ((2,3,6,7-tetramethyl-9,10-bis(trifluoromethyl)-9,10-dihydroanthracene-9,10-diyl)bis(oxy))bis(trimethylsilicane) (bis-TMS) (20.00 g, 36.4 mmol, 1.00 eq.) as a monomer was dissolved in THF (80 mL), and heated to the reflux temperature. Concentrated hydrochloric acid was slowly added, and the solution immediately became cloudy, and reacted by heating for 3 hours. The progress of the reaction was monitored. After complete reaction, the reaction solution was cooled to room temperature, and filtered under suction. The filter cake was washed with water (30 mL×3) and then washed with n-hexane (30 mL×3). The product was dried under vacuum, to obtain 2,3,6,7-tetramethyl-9,10-bis (trifluoromethyl)-9,10-dihydroanthracene-9,10-diol as a colorless crystal (yield 95%). $^1$H NMR (400 MHz, DMSO) δ7.68 (d, J=1.2 Hz, 1H), 7.26 (s, 1H), 2.31 (s, 3H).

Figure 2A:
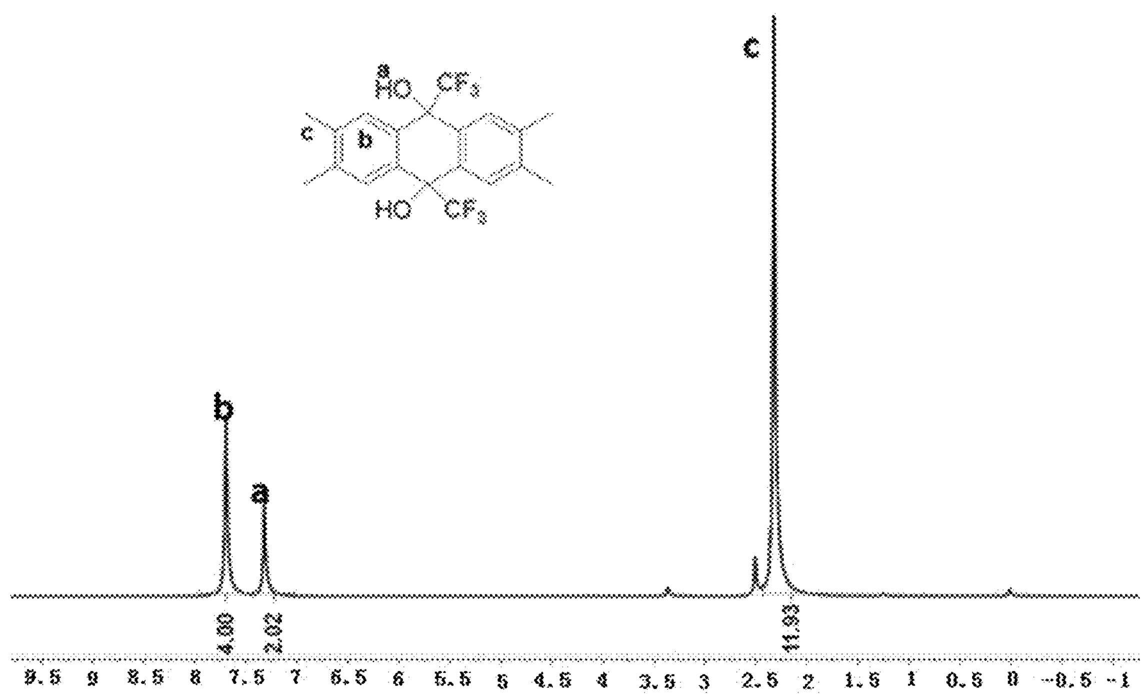
FIG. 2(*a*) is a $^1$H NMR spectrum of 2,3,6,7-tetramethyl-9,10-bis(trifluoromethyl)-9,10-dihydroanthracene-9,10-diol synthesized in Step 2 of Example 1.
Figure 2B:
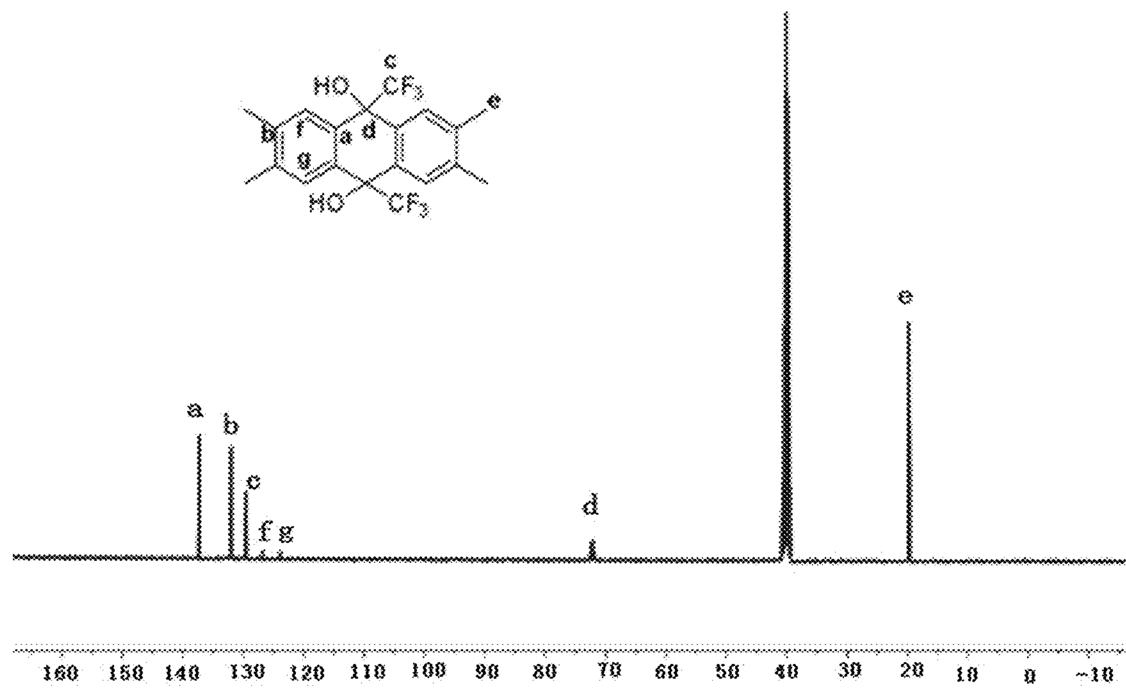

FIG. 2(*a*) is a $^1$H NMR spectrum of 2,3,6,7-tetramethyl-9,10-bis(trifluoromethyl)-9,10-dihydroanthracene-9,10-diol synthesized in Step 2 of Example 1; and FIG. 2(*b*) is a $^{13}$C NMR spectrum of 2,3,6,7-tetramethyl-9,10-bis(trifluoromethyl)-9,10-dihydroanthracene-9,10-diol synthesized in Step 2 of Example 1. As can be seen from FIG. 2, $^1$H NMR (600 MHz, DMSO-$d_6$) δ7.69 (d, J=1.2 Hz, 4H), 7.32 (s, 2H), 2.32 (s, 12H). $^{13}$C NMR (100 MHz, DMSO-$d_6$) δ137.26 (s), 131.90 (s), 129.46 (s), 72.11 (t, J=26.6 Hz), 19.84 (s). $^{19}$F NMR (565 MHz, DMSO-$d_6$) 6-76.69 (s, 6F). Therefore, the compound obtained in Step 2 is 2,3,6,7-tetramethyl-9,10-bis(trifluoromethyl)-9,10-dihydroanthracene-9,10-diol.

Step 3:2,3,6,7-tetramethyl-9,10-bis(trifluoromethyl)-9,10-dihydroanthracene-9,10-diol (10 g, 24.7 mmol, 1.00 eq.) was dissolved in anhydrous THF (30 mL), and cooled to −78° C. in the absence of water and oxygen. Diethylaminosulfur trifluoride (DAST) (7.23 mL, 54.4 mmol, 2.20 eq.) was slowly added dropwise, and then continuously reacted for 12 hrs. The progress of the reaction was monitored by Thin layer chromatography (TLC). After complete reaction, sodium bicarbonate was added to quench excess DAST. After quenching, the reaction solution was filtered, the filtrate was rotary dried, and separated by column chromatography. The product was recrystallized from n-hexane. The product was dried under vacuum, to obtain 9,10-difluoro-2,3,6,7-tetramethyl-9,10-bis(trifluoromethyl)-9,10-dihydroanthracene (yield 85%). $^1$H NMR (600 MHz, CDCl3) δ7.68 (d, J=26.0 Hz, 1H), 2.39 (s, 3H).

Figure 3A:
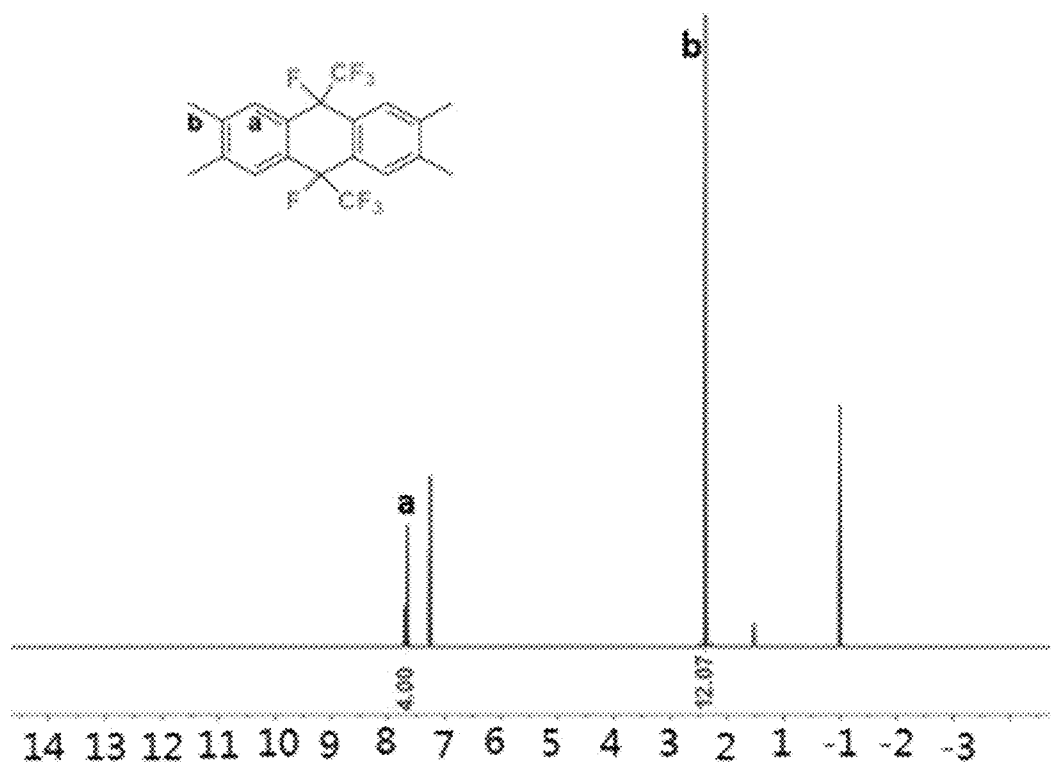
FIG. 3(*a*) is a $^1$H NMR spectrum of 9,10-difluoro-2,3,6,7-tetramethyl-9,10-bis(trifluoromethyl)-9,10-dihydroanthracene synthesized in Step 3 of Example 1.
Figure 3B:
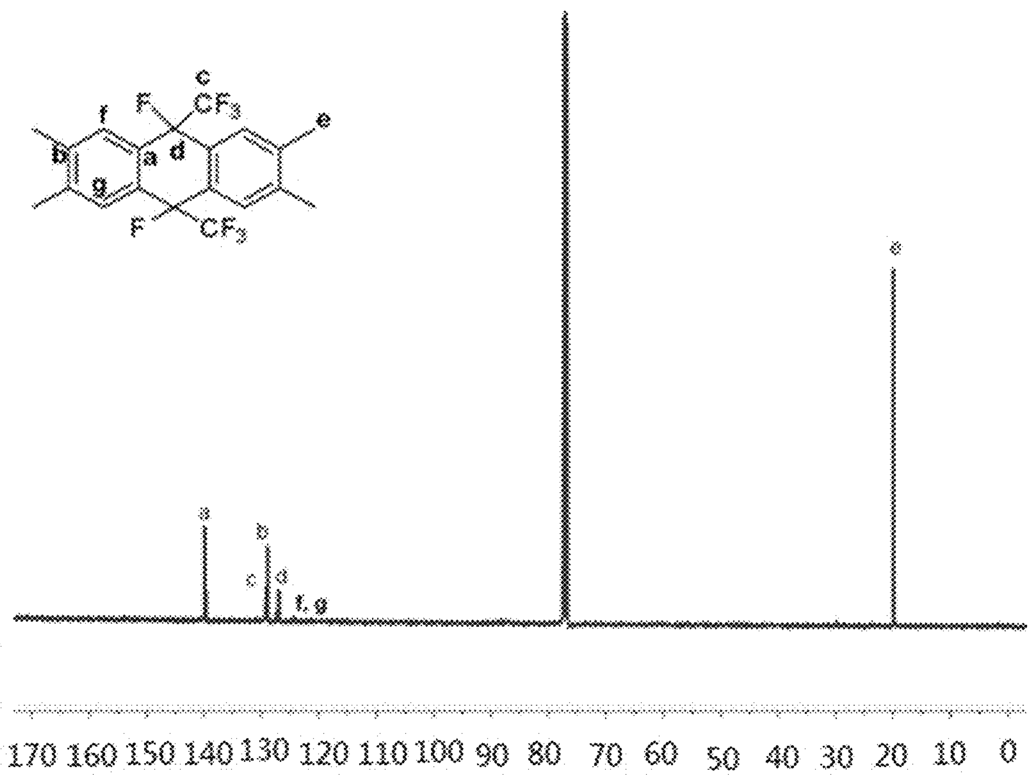

FIG. 3(*a*) is a $^1$H NMR spectrum of 9,10-difluoro-2,3,6,7-tetramethyl-9,10-bis(trifluoromethyl)-9,10-dihydroanthracene synthesized in Step 3 of Example 1; and FIG. 3(*b*) is a $^{13}$C NMR spectrum of 9,10-difluoro-2,3,6,7-tetramethyl-9,10-bis(trifluoromethyl)-9,10-dihydroanthracene synthesized in Step 3 of Example 1. As can be seen from FIG. 3, $^{1}$H NMR, CDCl3) δ7.68 (d, J=26.0 Hz, 4H), 2.39 (s, 12H). $^{13}$C NMR (100 MHz, CDCl3) δ139.87, 139.61, 129.18, 128.90, 127.44-126.52, 19.90. $^{19}$F NMR (565 MHz, CDCl3) δ−77.80 (d, 2F), −77.98 (m, 4F), −157.55 (m, 2F). Therefore the compound obtained in Step 3 is 9,10-difluoro-2,3,6,7-tetramethyl-9,10-bis(trifluoromethyl)-9,10-dihydroanthracene.

Step 4: 9,10-difluoro-2,3,6,7-tetramethyl-9,10-bis(trifluoromethyl)-9,10-dihydroanthracene (5 g, 12.2 mmol, 1.00 eq.) was dissolved in a solvent of pyridine and water (30 mL, vol/vol 1:1), and heated to the reflux temperature. Potassium permanganate (19.34 g, 0.122 mmol, 10.00 eq.) was weighed, and fed to a reaction flask portionwise in 1 hr. After the reaction was completed, the reaction solution was filtered under suction while hot, and the filtrate was rotary dried. The product was dissolved in hot water, acidified with concentrated hydrochloric acid, and filtered under suction to obtain a tetracarboxylic acid product. The product was recrystallized from acetic acid and dried under vacuum, to obtain 9,10-difluoro-9,10-bis(trifluoromethyl)-9,10-dihydroanthracene-2,3,6,7-tetracarboxylic acid (yield 85%). $^{1}$H NMR (600 MHz, DMSO) δ 13.98 (s, 1H), 8.53-7.94 (m, 1H).

Figure 4A:
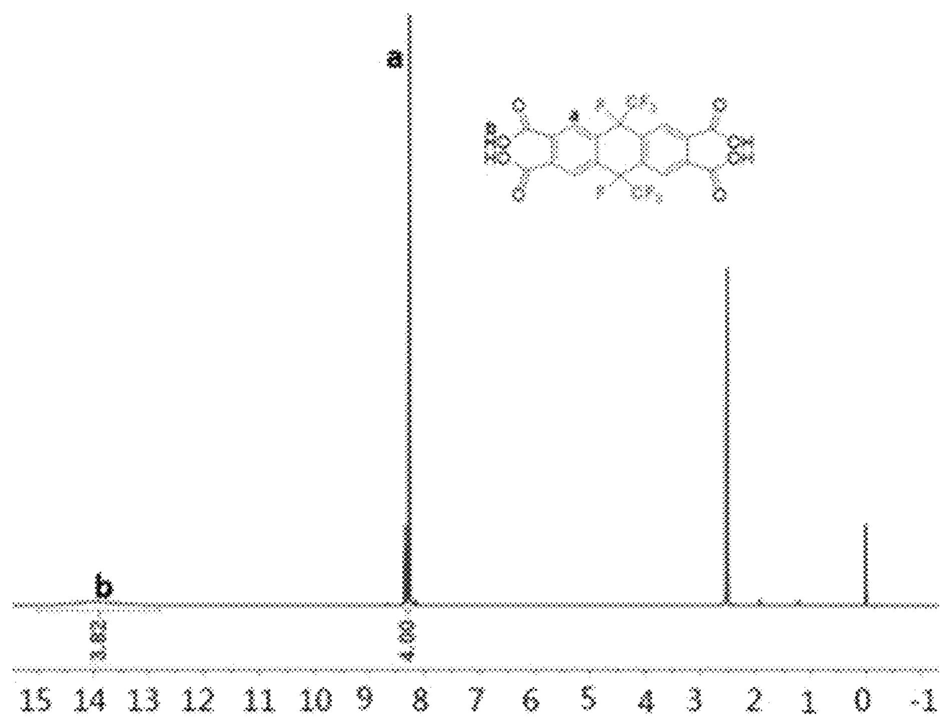
FIG. 4(*a*) is a $^1$H NMR spectrum of 9,10-difluoro-9,10-bis(trifluoromethyl)-9,10-dihydroanthracene-2,3,6,7-tetracarboxylic acid synthesized in Step 4 of Example 1.
Figure 4B:
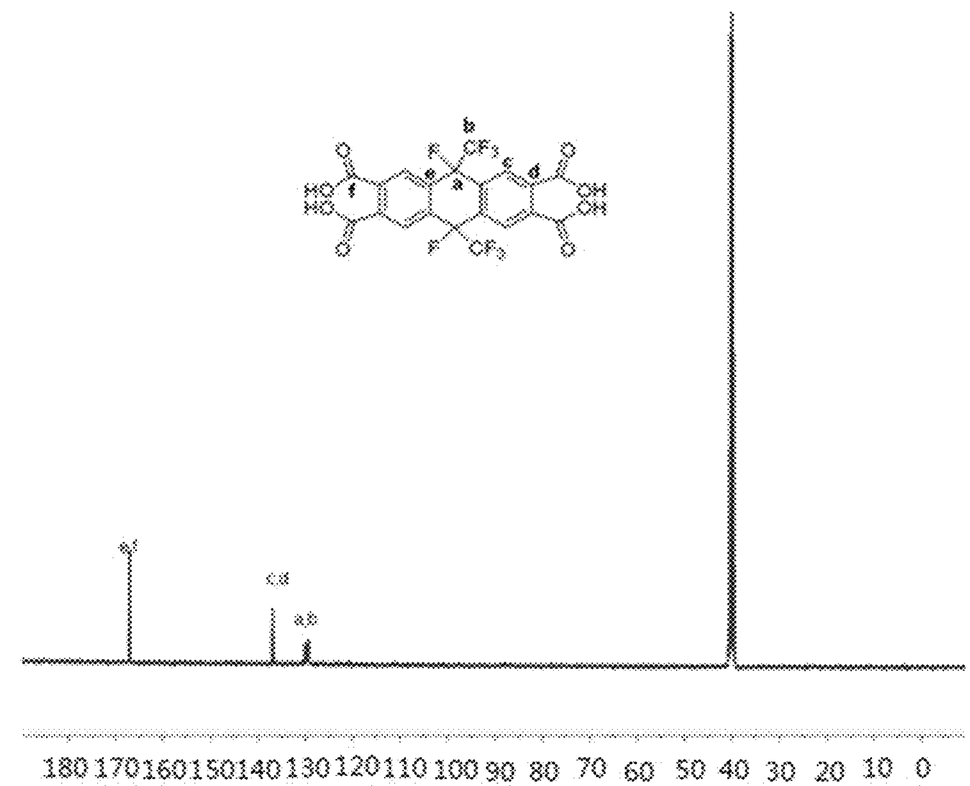

FIG. 4(*a*) is a $^{1}$H NMR spectrum of 9,10-difluoro-9,10-bis(trifluoromethyl)-9,10-dihydroanthracene-2,3,6,7-tetracarboxylic acid synthesized in Step 4 of Example 1; and FIG. 4(*b*) is a $^{13}$C NMR spectrum of 9,10-difluoro-9,10-bis(trifluoromethyl)-9,10-dihydroanthracene-2,3,6,7-tetracarboxylic acid synthesized in Step 4 of Example 1. As can be seen from FIG. 4, $^{1}$H NMR (600 MHz, DMSO-$d_6$) δ13.98 (s, 4H), 8.53-7.94 (m, 4H). $^{13}$C NMR (100 MHz, DMSO-$d_6$) δ167.05, 166.97, 136.90, 136.79-136.53, 130.00, 129.40. $^{19}$F NMR (565 MHz, DMSO-$d_6$) δ−76.31 (m, 6F), −142.23 (m, 2F). Therefore the compound obtained in Step 4 is 9,10-difluoro-9,10-bis(trifluoromethyl)-9,10-dihydroanthracene-2,3,6,7-tetracarboxylic acid.

Figure 8:
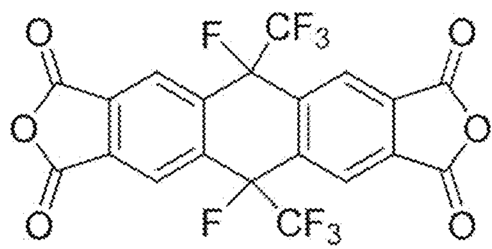
FIG. 8 shows a structural formula of the compound 9,10-difluoro-9,10-bis(trifluoromethyl)-9,10-dihydroanthracene-2,3,6,7-tetracarboxylic dianhydride provided in the present invention.

Step 5:9,10-difluoro-9,10-bis(trifluoromethyl)-9,10-dihydroanthracene-2,3,6,7-tetracarboxylic acid (5 g, 9.47 mmol, 1.00 eq.) was dissolved in acetic anhydride (30 mL), heated to the reflux temperature, and reacted for 10 hrs. The progress of the reaction was monitored by TLC. After complete reaction, the reaction solution was rotary dried, and then dried under vacuum to obtain 9,10-difluoro-9,10-bis(trifluoromethyl)-9,10-dihydroanthracene-2,3,6,7-tetracarboxylic dianhydride (yield 85%). $^{1}$H NMR (600 MHz, DMSO) δ8.83-8.63 (m, 1H), 8.34 (dd, J=43.5, 25.8 Hz, 1H). FIG. 8 shows a structural formula of the compound 9,10-difluoro-9,10-bis(trifluoromethyl)-9,10-dihydroanthracene-2,3,6,7-tetracarboxylic dianhydride prepared in the present invention.

Figure 5A:
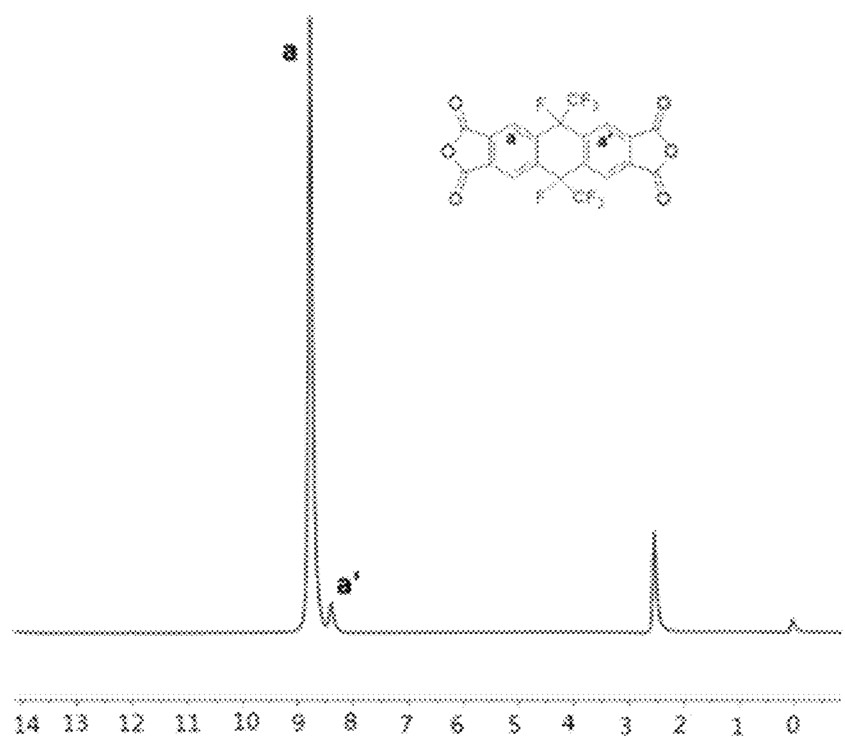
FIG. 5(*a*) is a $^1$H NMR spectrum of 9,10-difluoro-9,10-bis(trifluoromethyl)-9,10-dihydroanthracene-2,3,6,7-tetracarboxylic dianhydride synthesized in Step 5 of Example 1.
Figure 5B:
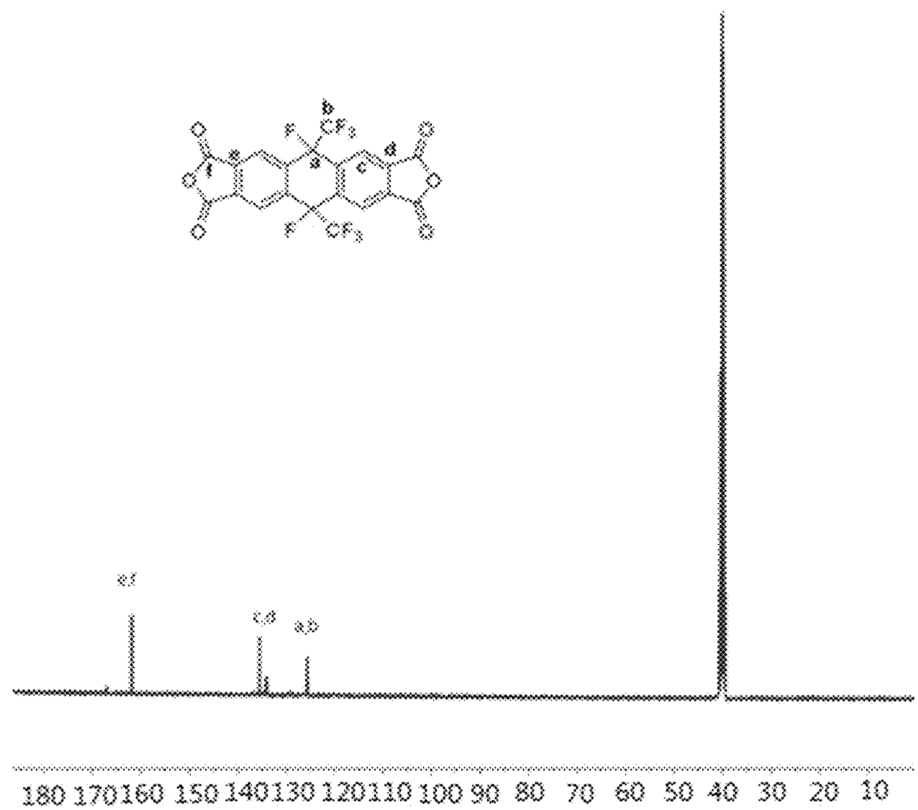
Figure 6A:
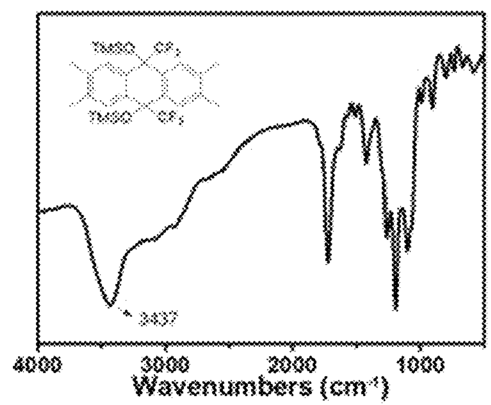
FIGS. 6(*a*), 6(*b*), 6(*c*), 6(*d*) and 6(*e*) are respectively an IR spectrum of the product synthesized in each of Steps 1 to 5 in Example 1.
Figure 6B:
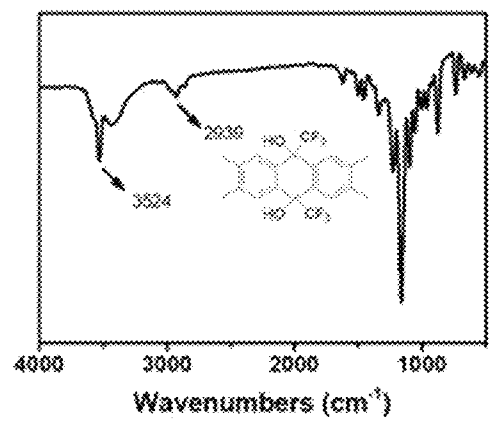
Figure 6C:
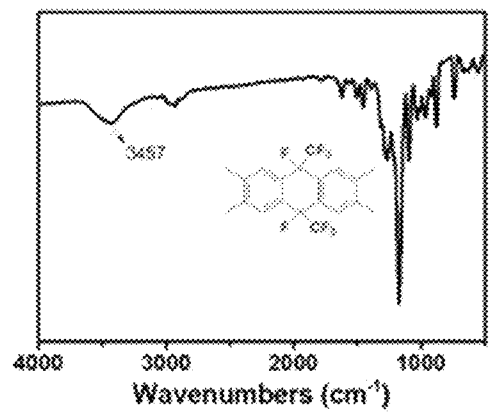
Figure 6D:
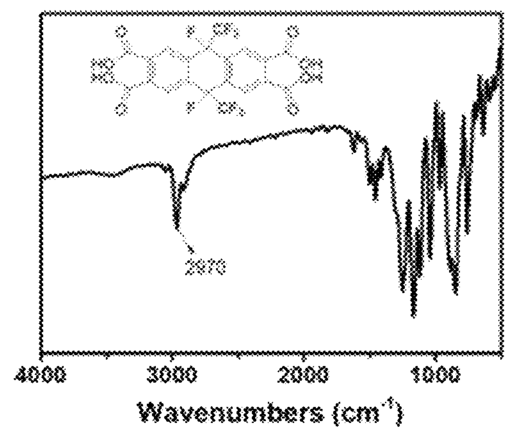
Figure 6E:
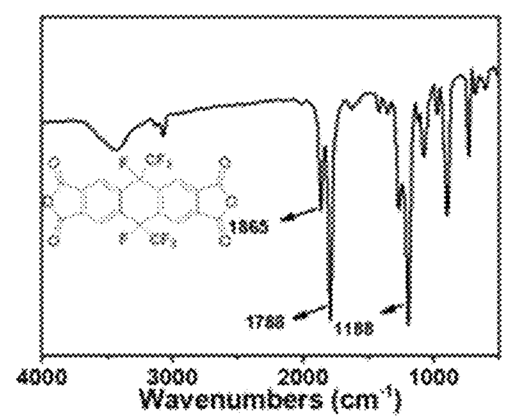

FIG. 5(*a*) is a $^{1}$H NMR spectrum of 9,10-difluoro-9,10-bis(trifluoromethyl)-9,10-dihydroanthracene-2,3,6,7-tetracarboxylic dianhydride synthesized in Step 5 of Example 1; and FIG. 5(*b*) is a $^{13}$C NMR spectrum of 9,10-difluoro-9,10-bis(trifluoromethyl)-9,10-dihydroanthracene-2,3,6,7-tetracarboxylic dianhydride synthesized in Step 5 of Example 1. As can be seen from FIG. 5, $^{1}$H NMR (600 MHz, DMSO-$d_6$) δ8.83-8.63 (m, 4H). $^{13}$C NMR (100 MHz, DMSO-$d_6$) δ161.87, 161.80, 135.42, 134.13, 125.73, 125.64. $^{19}$F NMR (565 MHz, DMSO-$d_6$) δ−75.64 (m, 6F), −139.35 (s, 2F). Therefore the compound obtained in Step 5 is 9,10-difluoro-9,10-bis(trifluoromethyl)-9,10-dihydroanthracene-2,3,6,7-tetracarboxylic dianhydride.

FIGS. 6(*a*), 6(*b*), 6(*c*), 6(*d*), and 6(*e*) are respectively an IR spectrum of the product synthesized in each of Steps 1 to 5 in Example 1.

Figure 7:
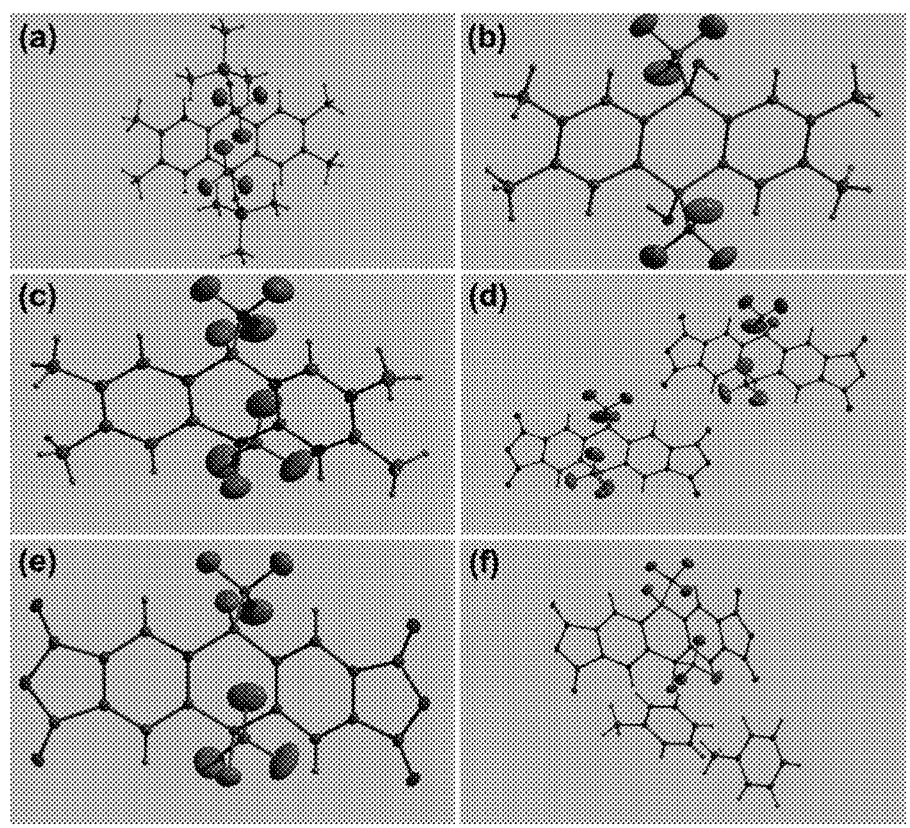
In FIG. 7, (a) is an X-ray diffraction pattern showing the spatial structure of the product as a single crystal synthesized in Step 1 of Example 1; (b) is an X-ray diffraction pattern showing the spatial structure of the product as a single crystal synthesized in Step 2 of Example 1; (c) is an X-ray diffraction pattern showing the spatial structure of the product as a single crystal synthesized in Step 3 of Example 1; (d) and (e) are X-ray diffraction patterns showing the spatial structure of the product synthesized in Step 5 of Example 1 in the form of a single crystal obtained after sublimation; and (f) is an X-ray diffraction pattern showing the spatial structure of the product synthesized in Step 5 of Example 1 in the form of a single crystal obtained after recrystallization in toluene.

In FIG. 7, (a) is an X-ray diffraction pattern showing the spatial structure of the product as a single crystal synthesized in Step 1 of Example 1; (b) is an X-ray diffraction pattern showing the spatial structure of the product as a single crystal synthesized in Step 2 of Example 1; (c) is an X-ray diffraction pattern showing the spatial structure of the product as a single crystal synthesized in Step 3 of Example 1; (d) and (e) are X-ray diffraction patterns showing the spatial structure of the product synthesized in Step 5 of Example 1 in the form of a single crystal obtained after sublimation; and (f) is an X-ray diffraction pattern showing the spatial structure of the product synthesized in Step 5 of Example 1 in the form of a single crystal obtained after recrystallization in toluene. It can be seen from FIG. 7 that a respective product is obtained in each step.

EXAMPLE 2

A method for preparing a dianhydride compound having a rigid alicyclic fluorine-containing structure, that is, 9,10-diphenyl-9,10-bis(trifluoromethyl)-9,10-dihydroanthracene-2,3,6,7-tetracarboxylic dianhydride, includes the following steps.

Steps 1 and 2 were as described in Example 1. 2,3,6,7-tetramethyl-9,10-bis(trifluoromethyl)-9,10-dihydroanthracene-9,10-diol was obtained.

Step 3: 2,3,6,7-tetramethyl-9,10-bis(trifluoromethyl)-9,10-dihydroanthracene-9,10-diol (200 mg, 0.5 mmol, 1 eq.) was dissolved in anhydrous THF (10 ml), and stirred. $PBr_3$ (0.23 ml, 3.45 mg, 0.013 mmol, 0.026 eq.) was injected, stirred for 10-30 min in the dark at room temperature, then heated to 50° C., reacted for 24 hr, and then cooled. The crude product was separated by column chromatography (n-pentane to n-pentane/MTBE 15:1), to obtain the compound 9,10-dibromo-2,3,6,7-tetramethyl-9,10-bis(trifluoromethyl)-9,10-dihydroanthracene. The yield was 95%.

Step 4: 9,10-dibromo-2,3,6,7-tetramethyl-9,10-bis(trifluoromethyl)-9,10-dihydroanthracene (40 mg, 0.075 mmol, 1 eq.) was dissolved in anhydrous THF (10 ml), 1,3-bis(diphenylphosphinopropane)nickel dichloride (2.03 mg, 0.0038 mmol, 0.05 eq.) was added, and then phenylmagnesium bromide (0.2 ml, 34 mg, 0.188 mmol, 2.5 eq.) was added dropwise, reacted at room temperature for 1 hr, then heated to the reflux temperature, and refluxed for 20-24 h. The reaction solution was cooled to room temperature, extracted with anhydrous diethyl ether, and separated by column chromatography (n-hexane), to obtain 2,3,6,7-tetramethyl-9,10-diphenyl-9,10-bis(trifluoromethyl)-9,10-dihydroanthracene (yield 50%).

Step 5: 2,3,6,7-tetramethyl-9,10-diphenyl-9,10-bis(trifluoromethyl)-9,10-dihydroanthracene (5 g, 9.5 mmol, 1.00 eq.) was dissolved in a solvent of pyridine and water (30 mL, vol/vol 1:1), and heated to the reflux temperature. Potassium permanganate (15.01 g, 95 mmol, 10.00 eq.) was weighed, and fed to a reaction flask portionwise in 1 hr. After the reaction was completed, the reaction solution was filtered under suction while hot, and the filtrate was rotary dried. The product was dissolved in hot water, acidified with concentrated hydrochloric acid, and filtered under suction to obtain a tetracarboxylic acid product. The product was recrystallized from acetic acid and dried under vacuum, to obtain 9,10-diphenyl-9,10-bis(trifluoromethyl)-9,10-dihydroanthracene-2,3,6,7-tetracarboxylic acid (yield 85%).

Step 6: 9,10-diphenyl-9,10-bis(trifluoroethyl)-9,10-dihydroanthracene-2,3,6,7-tetracarboxylic acid (5 g, 7.76 mmol, 1.00 eq.) was dissolved in acetic anhydride (30 mL), heated to the reflux temperature, and reacted for 10 hrs. The progress of the reaction was monitored by TLC. After complete reaction, the reaction solution was rotary dried, and then dried under vacuum to obtain 9,10-diphenyl-9,10-bis(trifluoromethyl)-9,10-dihydroanthracene-2,3,6,7-tetracarboxylic dianhydride (yield 85%).

Step 6: 9,10-diphenyl-9,10-bis(trifluoromethyl)-9,10-dihydroanthracene-2,3,6,7-tetracarboxylic acid (5 g, 7.76 mmol, 1.00 eq.) was dissolved in acetic anhydride (30 mL), heated to the reflux temperature, and reacted for 10 hrs. The progress of the reaction was monitored by TLC. After complete reaction, the reaction solution was rotary dried, and then dried under vacuum to obtain 9,10-diphenyl-9,10-bis(trifluoromethyl)-9,10-dihydroanthracene-2,3,6,7-tetracarboxylic dianhydride (yield 85%).

EXAMPLE 3

A method for preparing a dianhydride compound having a rigid alicyclic fluorine-containing structure, that is, 9,10-dichloro-9,10-bis(trifluoromethyl)-9,10-dihydroanthracene-2,3,6,7-tetracarboxylic dianhydride, includes the following steps.

Steps 1 and 2 were as described in Example 1,2,3,6,7-tetramethyl-9,10-bis(trifluoromethyl)-9,10-dihydroanthracene-9,10-diol was obtained.

Step 3:2,3,6,7-tetramethyl-9,10-bis(trifluoromethyl)-9,10-dihydroanthracene-9,10-diol (200 mg, 0.5 mmol, 1 eq.) was dissolved in toluene (15 ml), and acetyl chloride (98.125 mg, 1.25 mmol, 2.5 eq.) was then added, stirred for 10 min at room temperature, then heated to 75° C., and reacted for 8 hr. The reaction solution was cooled to room temperature, and separated by column chromatography to obtain the product 9,10-dichloro-2,3,6,7-tetramethyl-9,10-bis(trifluoromethyl)-9,10-dihydroanthracene (yield 65%).

Step 4: 9,10-dichloro-2,3,6,7-tetramethyl-9,10-bis(trifluoromethyl)-9,10-dihydroanthracene (5 g, 11.3 mmol, 1.00 eq.) was dissolved in a solvent of pyridine and water (30 mL, vol/vol 1:1), and heated to the reflux temperature. Potassium permanganate (21.4 g, 135.6 mmol, 12.00 eq.) was weighed, and fed to a reaction flask portionwise in 1 hr. After the reaction was completed, the reaction solution was filtered under suction while hot, and the filtrate was rotary dried. The product was dissolved in hot water, acidified with concentrated hydrochloric acid, and filtered under suction to obtain a tetracarboxylic acid product. The product was recrystallized from acetic acid and dried under vacuum, to obtain 9,10-dichloro-9,10-bis(trifluoromethyl)-9,10-dihydroanthracene-2,3,6,7-tetracarboxylic acid (yield 85%).

Step 5: 9,10-dichloro-9,10-bis(trifluoromethyl)-9,10-dihydroanthracene-2,3,6,7-tetracarboxylic acid (5 g, 8.9 mmol, 1.00 eq.) was dissolved in acetic anhydride (30 mL), heated to the reflux temperature, and reacted for 10 hrs. The progress of the reaction was monitored by TLC. After complete reaction, the reaction solution was rotary dried, and then dried under vacuum to obtain 9,10-dichloro-9,10-bis(trifluoromethyl)-9,10-dihydroanthracene-2,3,6,7-tetracarboxylic dianhydride (yield 85%).

EXAMPLE 4

A method for preparing a dianhydride compound having a rigid alicyclic fluorine-containing structure, that is, 9,9',10,10'-tetrakis(trifluoromethyl)-9,10-dihydroanthracene-2,3,6,7-tetracarboxylic dianhydride, includes the following steps.

Steps 1 and 2 were as described in Example 1. 2,3,6,7-tetramethyl-9,10-bis(trifluoromethyl)-9,10-dihydroanthracene-9,10-diol was obtained.

Step 3: Under nitrogen atmosphere, 2,3,6,7-tetramethyl-9,10-bis(trifluoromethyl)-9,10-dihydroanthracene-9,10-diol (200 mg, 0.5 mmol, 1 eq.) was dissolved in THF (10 ml), hydrogen iodide (0.17 ml, 190 mg, 1.5 mmol, 3 eq.) was added, and then trifluoromethyl iodide (293.85 mg, 1.5 mmol, 3 eq.) was added, reacted at room temperature for 24 hrs, and then separated by column chromatography, to obtain 2,3,6,7-tetramethyl-9,9',10,10'-tetrakis(trifluoromethyl)-9,10-dihydroanthracene.

Step 4: 2,3,6,7-tetramethyl-9,9',10,10'-tetrakis(trifluoromethyl)-9,10-dihydroanthracene (5 g, 9.84 mmol, 1.00 eq.) was dissolved in a solvent of pyridine and water (30 mL, vol/vol 1:1), and heated to the reflux temperature. Potassium permanganate (18.66 g, 118.08 mmol, 12.00 eq.) was weighed, and fed to a reaction flask portionwise in 1 hr. After the reaction was completed, the reaction solution was filtered under suction while hot, and the filtrate was rotary dried. The product was dissolved in hot water, acidified with concentrated hydrochloric acid, and filtered under suction to obtain a tetracarboxylic acid product. The product was recrystallized from acetic acid and dried under vacuum, to obtain 9,9',10,10'-tetrakis(trifluoromethyl)-9,10-dihydroanthracene-2,3,6,7-tetracarboxylic acid (yield 85%).

Step 5:9,9',10,10'-tetrakis(trifluoromethyl)-9,10-dihydroanthracene-2,3,6,7-tetracarboxylic acid(5 g, 7.96 mmol, 1.00 eq.) was dissolved in acetic anhydride (30 mL), heated to the reflux temperature, and reacted for 10 hrs. The progress of the reaction was monitored by TLC. After complete reaction, the reaction solution was rotary dried, and then dried under vacuum to obtain 9,9',10,10'-tetrakis(trifluoromethyl)-9,10-dihydroanthracene-2,3,6,7-tetracarboxylic dianhydride (yield 80%).

EXAMPLE 5

A polyimide was synthesized with the dianhydride compound 9,10-difluoro-9,10-bis(trifluoromethyl)-9,10-dihydroanthracene-2,3,6,7-tetracarboxylic dianhydride prepared in Example 1 through the following steps.

Step 1: PPDA (3 mmol) was dissolved in an appropriate amount of dry NMP in a 50 mL flask, and then 8FDA (3 mmol) was slowly added in one portion to the above solution in which the diamine was dissolved. The reaction was stirred at 25° C. for 24 hours to obtain a polyamic acid (PAA) solution.

Step 2: The polyamic acid solution was poured onto clean glass that was thoroughly washed with ITO glass cleaner and deionized water and dried, and then PAA was uniformly dispersed on the glass surface by casting. Next, the casted PAA/glass was placed in an oven preheated to 80° C. The casted PAA/glass was heated at 80° C. for 2 hours to slowly release the solvent, and then heated according to the temperature program of 100° C. for 1 hour, 150° C. for 1 hour, 200° C. for 1 hour, 250° C. for 1 hour, and 280° C. for 1 hour. After the temperature in the oven was naturally cooled to room temperature, a line was drawn at the edge of the film with a scalpel, and after being immersed in deionized water, the film was peeled off from the surface of the glass.

A thermally imidized polyimide film was obtained.

EXAMPLE 6

The polyimide film obtained in Example 5 was evaluated for the thermal and mechanical properties of the PI film by thermogravimetric analysis (TGA), dynamic mechanical analysis (DMA) and thermomechanical analysis (TMA). Thermogravimetric analysis (TGA) was performed with a Perkin-Elmer TGA-2 at a heating rate of 10° C./min under a nitrogen stream. Dynamic mechanical analysis was carried out with DMA Q800 V20.22 Build 41 in tensile mode at a frequency of 1 Hz. The coefficient of thermal expansion was tested with the TA Instrument Q400. Nitrogen flow: 0.05N. Heating rate: 5° C./minute.

Figure 10:
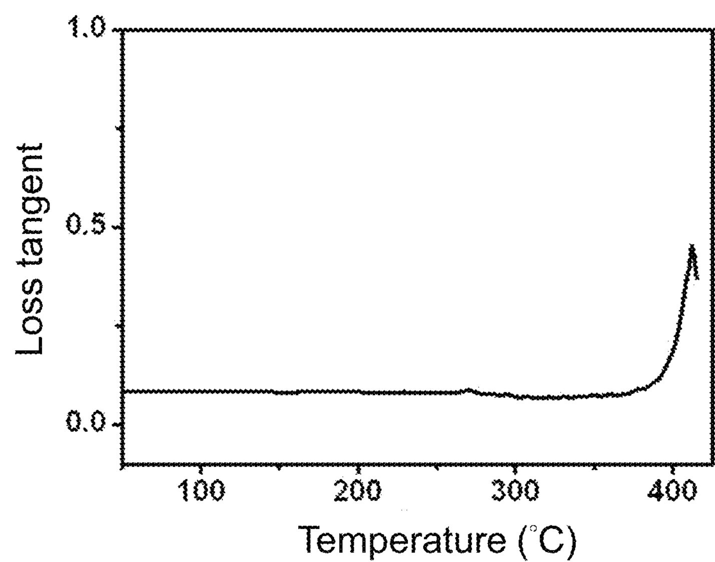
FIG. 10 is a DMA curve of a PI film.
Figure 11:
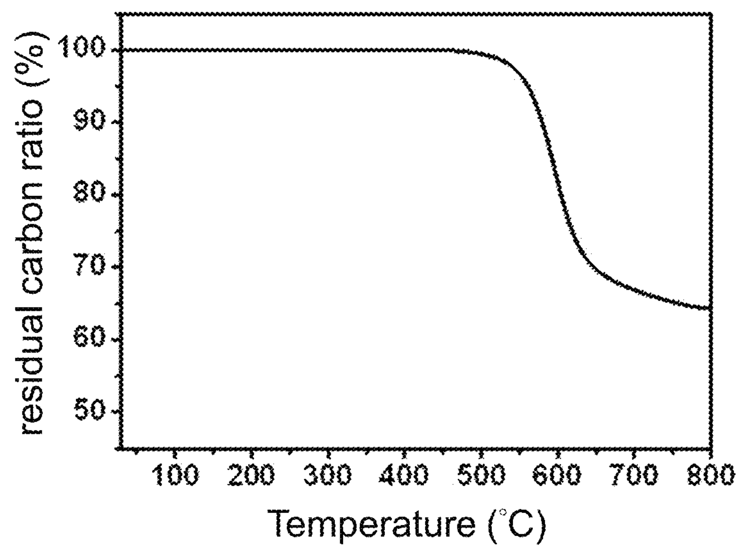
FIG. 11 is a TGA curve of a PI film.
Figure 12:
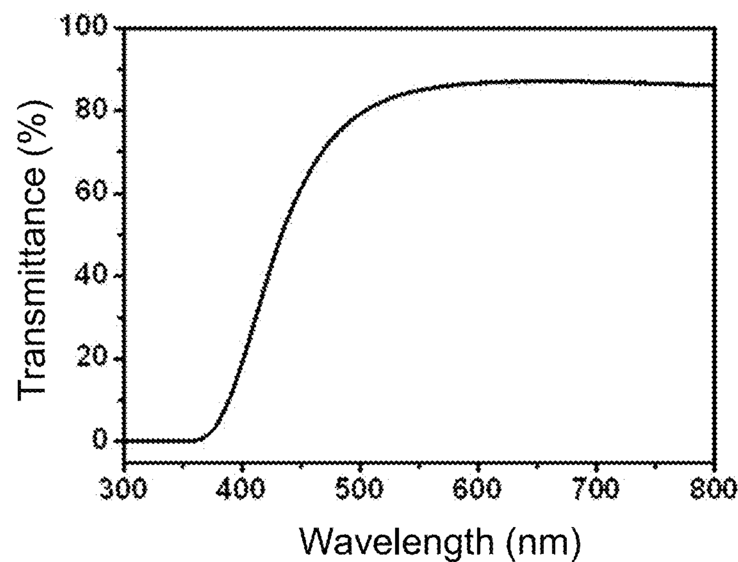
FIG. 12 is a transmittance curve of a PI film.
Figure 13:
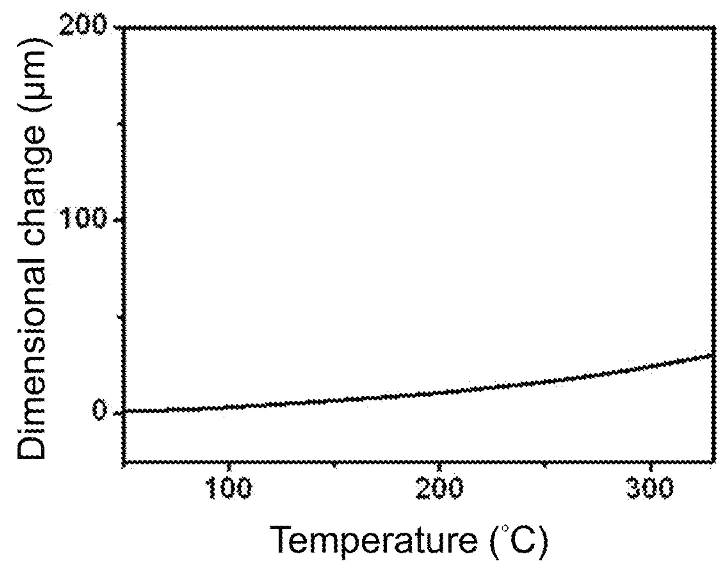
FIG. 13 is a TMA curve of a PI film.

The test results are shown in Table 1. FIG. 10 shows the DMA curve of the PI film; and FIG. 11 shows the TGA curve of the PI film. FIG. 12 shows the transmittance curve of the PI film. FIG. 13 shows the TMA curve of the PI film.

According to the DMA curve in FIG. 10, the Tg value of the PI film based on the dianhydride compound (8FDA) having a rigid alicyclic fluorine-containing structure of the present invention is 414° C. The Tg value of the PI film based on 4,4'-(hexafluoroisopropylidene)diphthalic anhydride (6FDA) is 332° C. This is attributed to the rigid structure of the dianhydride compound (8FDA) monomer having a rigid alicyclic fluorine-containing structure of the present invention. The $T_g$ value of the polyimide is determined by the degree of rigidity of the molecular chain, and the CTC molecular interaction between the electron-withdrawing dianhydride residue and the electron-donating diamine residue. FIG. 11 shows the TGA curve of the PI film. The 1% thermal decomposition temperature ($T_{d1}$) and residue carbon ratio of polyimide are 500-517° C. and 65-66%. The PIs based on the dianhydride compound (8FDA) having a rigid alicyclic fluorine-containing structure of the present invention have a higher $T_{d1}$ value than a film of corresponding 4,4'-(hexafluoroisopropylidene)diphthalic anhydride (6FDA) (517° C. vs 500° C.). The polyimide based on the dianhydride compound (8FDA) having a rigid alicyclic fluorine-containing structure of the present invention is polysubstituted and has rigid semi-alicyclic 1,4-cyclohexadiene, and the rigidity of the molecular chain is higher than that of 4,4'-(hexafluoroisopropylidene)diphthalic anhydride (6FDA), and the interaction and accumulation between the chains are enhanced to increase the heat resistance. Compared to other films, PPDA derived from the dianhydride compound (8FDA) having a rigid alicyclic fluorine-containing structure of the present invention shows a relatively low transmittance (T % <30%) at 400 nm, as shown in FIG. 12. From these test results, it is found that PI-1 obtained through polymerization of the dianhydride compound (8FDA) having a rigid alicyclic fluorine-containing structure of the present invention and PPDA has excellent thermal stability and dimensional stability (where $T_g$ is 414° C., and CTE is 12 ppm $K^{-1}$), and has a $T_{450}$ that is close to 80%. FIG. 13 shows the TMA curve of the PI film. The PI film prepared by this method has a CTE value of 12 ppm $K^{-1}$. The currently available film based on 4,4'-(hexafluoroisopropylidene)diphthalic anhydride (6FDA) has a CTE of 47 ppm $K^{-1}$. Compared with 4,4'-(hexafluoroisopropylidene)diphthalic anhydride (6FDA), the CTE value of the film based on the dianhydride compound (8FDA) having a rigid alicyclic fluorine-containing structure of the present invention is significantly lower than that of a film based on 4,4'-(hexafluoroisopropylidene)diphthalic anhydride (6FDA). This can also be attributed to the more rigid structure of the dianhydride compound (8FDA) having a rigid alicyclic fluorine-containing structure of the present invention which can increase the intrachain orientation, and result in stronger intermolecular interactions that will inhibit the molecular motion and lead to the occurrence of lower CTE and better dimensional stability.

TABLE 1

Summary of thermal stability, mechanical and optical performance data of PIs based on 8FDA

| | Thermal stability | | | | | Mechanical performance | | | Optical performance | |
|---|---|---|---|---|---|---|---|---|---|---|
| | $T_g$(° C.) DMA | $T_{d1}$ (° C.) | $T_{d5}$ (° C.) | Residue carbon ratio (%) | CTE (ppm $K^{-1}$) | Ts (MPa) | Eb (%) | Tm (GPa) | $T_{400}$ (%) | $\lambda_0$ (nm) |
| PI | 414 | 517 | 556 | 65 | 12 | 109 | 2.6 | 4.1 | 19 | 368 |

The present invention has been described in detail with reference to preferred embodiments, which however are not intended to limit the present invention. Any modifications, equivalent improvements and substitutions can be made without departing from the spirit and principle of the present invention, which are all fall within the protection scope of the present invention.

What is claimed is:

1. A dianhydride compound having a rigid alicyclic fluorine-containing structure, represented by a structural Formula I below:

Formula (I)

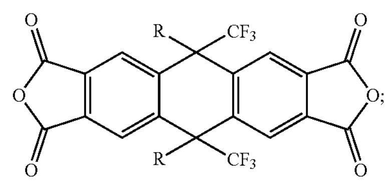

R is F, Cl, $CF_3$ or

.

2. A method for preparing a dianhydride compound having a rigid alicyclic fluorine-containing structure, comprising the steps of:

(1) adding trimethyl(trifluoromethyl)silicane or triethyl (trifluoromethyl)silicane to a solution of 2,3,6,7-tetramethylanthracene-9,10-dione, cooling, adding a catalyst A, mixing well until uniform, then heating the reaction temperature to 30-50° C., and reacting for 6-24 hrs, to allow the 2,3,6,7-tetramethylanthracene-9,10-dione to undergo a nucleophilic addition reaction, to obtain ((2,3,6,7-tetramethyl-9,10-bis(trifluoromethyl)-9,10-dihydroanthracene-9,10-diyl)bis(oxy))bis(trimethylsilicane);

(2) dissolving the ((2,3,6,7-tetramethyl-9,10-bis(trifluoromethyl)-9,10-dihydroanthracene-9,10-diyl)bis(oxy)) bis(trimethylsilicane) obtained in the step (1) and then reacting for 0.5-5 h in an acidic environment at a temperature of 25-80° C., to convert the trimethylsiloxane on the ((2,3,6,7-tetramethyl-9,10-bis(trifluoromethyl)-9,10-dihydroanthracene-9,10-diyl)bis(oxy)) bis(trimethylsilicane) into a hydroxyl group, to obtain 2,3,6,7-tetramethyl-9,10-bis(trifluoromethyl)-9,10-dihydroanthracene-9,10-diol;

(3) dissolving the 2,3,6,7-tetramethyl-9,10-bis(trifluoromethyl)-9,10-dihydroanthracene-9,10-diol obtained in the step (2), adding diethylaminosulfur trifluoride or bis(2-methoxyethyl)aminosulfur trifluoride dropwise in an ice bath, and reacting for 12-15 h, to obtain 9,10-difluoro-2,3,6,7-tetramethyl-9,10-bis(trifluoromethyl)-9,10-dihydroanthracene;

or (3) dissolving the 2,3,6,7-tetramethyl-9,10-bis(trifluoromethyl)-9,10-dihydroanthracene-9,10-diol obtained in the step (2), adding acetyl chloride, and reacting for 8-12 h at 70-80° C., to obtain 9,10-dichloro-2,3,6,7-tetramethyl-9,10-bis(trifluoromethyl)-9,10-dihydroanthracene;

or (3) dissolving the 2,3,6,7-tetramethyl-9,10-bis(trifluoromethyl)-9,10-dihydroanthracene-9,10-diol obtained in the step (2), adding hydrogen halide and trifluoromethyl halide, and reacting for 15-30 h, to obtain 2,3,6,7-tetramethyl-9,9',10,10'-tetrakis(trifluoromethyl)-9,10-dihydroanthracene;

or (3) dissolving the 2,3,6,7-tetramethyl-9,10-bis(trifluoromethyl)-9,10-dihydroanthracene-9,10-diol obtained in the step (2), followed by a first step of adding phosphorus tribromide, or adding hydrogen bromide and a catalyst B, and reacting for 12-24 h at 40-60° C., to converting the hydroxyl group on the 2,3,6,7-tetramethyl-9,10-bis(trifluoromethyl)-9,10-dihydroanthracene-9,10-diol into a bromine atom, to obtain 9,10-dibromo-2,3,6,7-tetramethyl-9,10-bis (trifluoromethyl)-9,10-dihydroanthracene; and a second step of adding phenylmagnesium bromide and a catalyst C, or adding phenylboronic acid and a catalyst D, and reacting for 8-15 h at 75-90° C., to replace the bromine atom on the 9,10-dibromo-2,3,6,7-tetramethyl-9,10-bis(trifluoromethyl)-9,10-dihydroanthracene by a phenyl group, to obtain 2,3,6,7-tetramethyl-9,10-diphenyl-9,10-bis(trifluoromethyl)-9,10-dihydroanthracene;

(4) dissolving the 9,10-difluoro-2,3,6,7-tetramethyl-9,10-bis(trifluoromethyl)-9,10-dihydroanthracene, 9,10-dichloro-2,3,6,7-tetramethyl-9,10-bis(trifluoromethyl)-9,10-dihydroanthracene, 2,3,6,7-tetramethyl-9,9',10,10'-tetrakis(trifluoromethyl)-9,10-dihydroanthracene, or 2,3,6,7-tetramethyl-9,10-diphenyl-9,10-bis(trifluoromethyl)-9,10-dihydroanthracene obtained in the step (3), adding an oxidant, reacting for 12-15 h at 90-110° C., filtering under suction, rotary drying the filtrate, dissolving the product, and acidifying, to obtain 9,10-difluoro-9,10-bis(trifluoromethyl)-9,10-dihydroanthracene-2,3,6,7-tetracarboxylic acid, 9,10-dichloro-9,10-bis(trifluoromethyl)-9,10-dihydroanthracene-2,3,6,7-tetracarboxylic acid, 9,9',10,10'-tetrakis(trifluoromethyl)-9,10-dihydroanthracene-2,3,6,7-tetracarboxylic acid or 9,10-diphenyl-9,10-bis(trifluoromethyl)-9,10-dihydroanthracene-2,3,6,7-tetracarboxylic acid; and (5) dehydrating the 9,10-difluoro-9,10-bis(trifluoromethyl)-9,10-dihydroanthracene-2,3,6,7-tetracarboxylic acid, 9,10-dichloro-9,10-bis(trifluoromethyl)-9,10-dihydroanthracene-2,3,6,7-tetracarboxylic acid, 9,9',10,10'-tetrakis(trifluoromethyl)-9,10-dihydroanthracene-2,3,6,7-tetracarboxylic acid or 9,10-diphenyl-9,10-bis (trifluoromethyl)-9,10-dihydroanthracene-2,3,6,7-tetracarboxylic acid obtained in the step (4) into an anhydride, to obtain 9,10-difluoro-9,10-bis(trifluoromethyl)-9,10-dihydroanthracene-2,3,6,7-tetracarboxylic dianhydride, 9,10-dichloro-9,10-bis(trifluoromethyl)-9,10-dihydroanthracene-2,3,6,7-tetracarboxylic dianhydride, 9,9',10,10'-tetrakis(trifluoromethyl)-9,10-dihydroanthracene-2,3,6,7-tetracarboxylic dianhydride or 9,10-diphenyl-9,10-bis(trifluoromethyl)-9,10-dihydroanthracene-2,3,6,7-tetracarboxylic dianhydride.

3. The method for preparing a dianhydride compound having a rigid alicyclic fluorine-containing structure according to claim 2, wherein the catalyst A in the step (1) is cesium fluoride, tetrabutylammonium fluoride or tris(dimethylamino)sulfonium difluorotrimethylsilicate; the catalyst B in the step (3) is concentrated sulfuric acid; the catalyst C in the step (3) is 1,3-bis(diphenylphosphinopropane)nickel dichloride, or a mixture of palladium acetate and triphenylphosphine; the catalyst D in the step (3) is a mixture of tetrakis(triphenylphosphine)palladium and potassium carbonate, or a mixture of palladium and potassium carbonate, or a mixture of sodium tetrachloropalladate and potassium carbonate; and the oxidant in the step (4) is potassium permanganate or chromium trioxide.

4. The method for preparing a dianhydride compound having a rigid alicyclic fluorine-containing structure according to claim 2, wherein the hydrogen halide in the step (3) is hydrogen bromide, hydrogen iodide or hydrogen chloride; and the trifluoromethyl halide in the step (3) is trifluoromethyl bromide, trifluoromethyl iodide or trifluoromethyl chloride.

5. The method for preparing a dianhydride compound having a rigid alicyclic fluorine-containing structure according to claim 2, wherein a ratio of amount of substances of 2,3,6,7-tetramethylanthracene-9,10-dione, trimethyl(trifluoromethyl)silicane and the catalyst A in the step (1) is 1:(2-3.5):(0.01-0.05).

6. The method for preparing a dianhydride compound having a rigid alicyclic fluorine-containing structure according to claim 2, wherein a ratio of amount of substances of 2,3,6,7-tetramethyl-9,10-bis(trifluoromethyl)-9,10-dihydroanthracene-9,10-diol to diethylaminosulfur trifluoride, or to bis(2-methoxyethyl)aminosulfur trifluoride in the step (3) is 1:(2-3.5).

7. The method for preparing a dianhydride compound having a rigid alicyclic fluorine-containing structure according to claim 2, wherein a ratio of amount of substances of 9,10-difluoro-2,3,6,7-tetramethyl-9,10-bis(trifluoromethyl)-9,10-dihydroanthracene, 9,10-dichloro-2,3,6,7-tetramethyl-9,10-bis(trifluoromethyl)-9,10-dihydroanthracene, 2,3,6,7-tetramethyl-9,9',10,10'-tetrakis(trifluoromethyl)-9,10-dihydroanthracene or 2,3,6,7-tetra ethyl-9,10-diphenyl-9,10-bis (trifluoromethyl)-9,10-dihydroanthracene to the oxidant in the step (4) is 1:(10-12).

8. A method for preparing a polyimide material, comprising:

using the dianhydride compound having a rigid alicyclic fluorine-containing structure according to claim 1 to react with a diamine in order to obtain a polyamic acid solution; and heating the polyamic acid solution.

9. A method for preparing a polyimide film, comprising the steps of (1) dissolving a diamine, adding the dianhydride compound having a rigid alicyclic fluorine-containing structure according to claim 1, and reacting for 10-30 h at 25-35° C., to obtain a polyamic acid solution; and (2) dispersing the polyamic acid solution obtained in the step (1) uniformly on the surface of the substrate, heating to volatilize the solvent in the polyamic acid solution, and further heating to cause dehydration and cyclization of the polyamic acid to obtain a polyimide film.

10. A polyimide film prepared through the method according to claim 9.

* * * * *